United States Patent [19]

Yamaguchi et al.

[11] Patent Number: 5,352,763
[45] Date of Patent: Oct. 4, 1994

[54] BIODEGRADABLE OPTICALLY ACTIVE POLYMERS AND INTERMEDIATE OLIGOMERS THEREOF, AND PROCESS FOR PRODUCING THEM

[75] Inventors: Akio Yamaguchi; Yoji Hori, both of Tokyo; Takashi Imai; Motoki Suzuki, both of Kanagawa; Susumu Akutagawa, Tokyo, all of Japan

[73] Assignee: Takasago International Corporation, Tokyo, Japan

[21] Appl. No.: 5,081

[22] Filed: Jan. 15, 1993

[30] Foreign Application Priority Data

Jan. 17, 1992 [JP] Japan .................................. 4-026262

[51] Int. Cl.$^5$ ............................................... C08G 63/06
[52] U.S. Cl. ..................................... 528/361; 549/267
[58] Field of Search ......................... 528/361; 549/267

[56] References Cited

FOREIGN PATENT DOCUMENTS 0491171 6/1992 European Pat. Off. .

OTHER PUBLICATIONS

CA104(12):95434x Henry, Earl Webb; "Nerve Regeneration Through Biodegradabe Polyester Tubes;" Dept. Neurosci., Child Hosp.

Primary Examiner—John Kight, III
Assistant Examiner—Terressa Mosley
Attorney, Agent, or Firm—Sughrue, Mion, Zinn, Macpeak & Seas

[57] ABSTRACT

An optically active oligomer obtained by polycondensation of an (R)-3-hydroxyalkanoic acid alkyl ester and at least one of a diol, a diamine and an amino alcohol and an optically active polymer obtained by copolymerization of said oligomer and a monomer selected from diisocyanic acid esters, dicarboxylic acid derivatives, and dichlorosilanes are disclosed. Novel functional polymers with biodegradability and hydrolyzability are produced with industrial advantage.

2 Claims, 1 Drawing Sheet

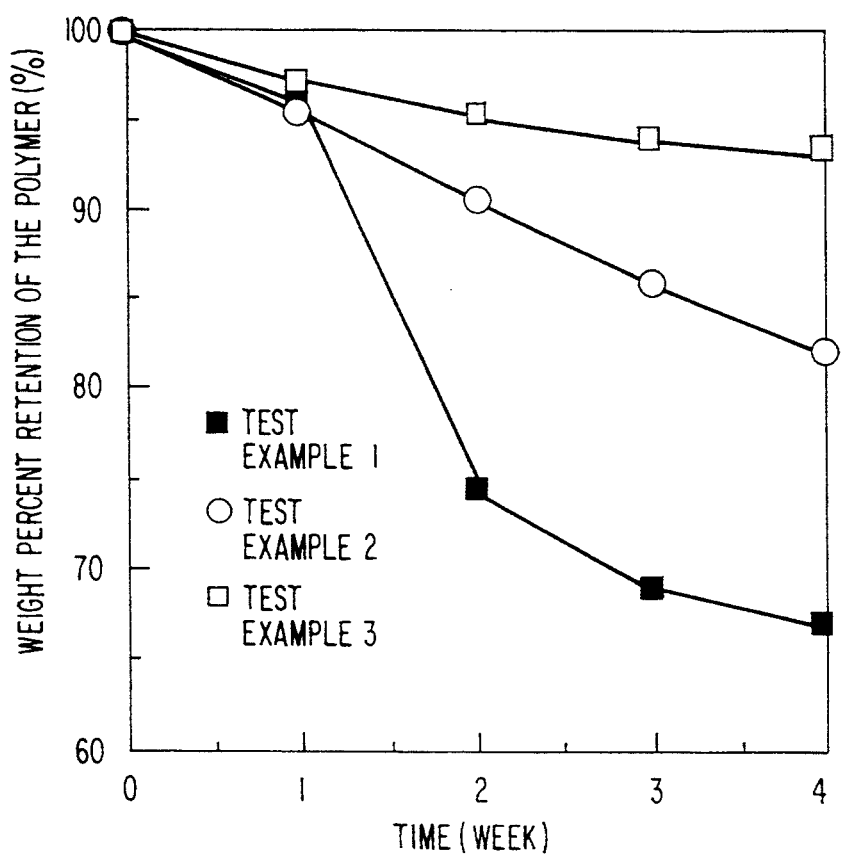
FIGURE

BIODEGRADABLE OPTICALLY ACTIVE POLYMERS AND INTERMEDIATE OLIGOMERS THEREOF, AND PROCESS FOR PRODUCING THEM

FIELD OF THE INVENTION

This invention relates to a biodegradable optically active polymer, a process for producing the polymer, an oligomer as an intermediate for the polymer, and a process for producing the oligomer. More particularly, it relates to an optically active oligomer having an (R)-3-hydroxyalkanoic acid ester (hereinafter abbreviated as (R)-3HA) unit and a process for producing the same, and to a biodegradable optically active polymer obtained by copolymerizing the oligomer with a monomer, and a process for producing the polymer.

The polyester, polyester-polyether, polyester-polyurethane, and polyester-polyether-polyurethane according to the present invention are functional thermoplastic resins having optical activity, biodegradability, and hydrolyzability which can be degraded by microorganisms in soil or water and therefore widely usable as clean plastics causing no environmental pollution.

BACKGROUND OF THE INVENTION

Microorganisms which accumulate polyester comprising (R)-3-hydroxybutyrate units (included in the (R)-3HA unit constituting the polymer of the present invention) in the microbial cells are known (see P. A. Holmes, *Phys. Technol.*, Vol. 16, p. 32 (1985)). This polymer has biodegradability, i.e., enzymatic decomposability, hydrolyzability, and bioaffinity, and is now attracting attention as a new type of functional material (see Yoshiharu Doi, *Seibunkaisei Kobunshi Zairyo*, page 19, Kogyo Chosakai (1990)). However, biological synthesis of a polymer utilizing a microorganism or an enzymatic reaction requires complicated steps such as separation of the polymer from microbial cells.

On the other hand, ring-open polymerization of D-(+)-methyl-$\beta$-propiolactone is reported in *Polymer Letters*, Vol. 9, p. 173 (1970). However, a convenient process for synthesizing D-(+)-methyl-$\beta$-propiolactone to be ring-open polymerized has not yet been established.

In addition, either of these known techniques involves various industrial problems, such as the high production cost incurred.

SUMMARY OF THE INVENTION

An object of the present invention is to provide a novel optically active biodegradable polymer comprising an (R)-3HA unit which is excellent in biodegradability and hydrolyzability.

Another object of the present invention is to provide an industrially advantageous process for producing such an optically active biodegradable polymer.

As a result of extensive investigations, the inventors have found that an optically active oligomer having an (R)-3HA unit is easily copolymerized with a monomer in the presence of a catalyst to provide a corresponding optically active polymer.

The present invention relates to an optically active polymer represented by formula (II):

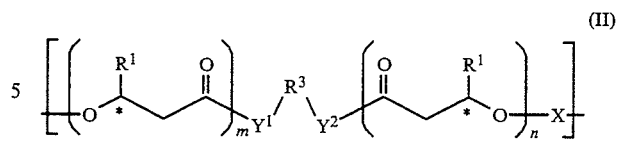

wherein $R^1$ represents an alkyl group having from 1 to 5 carbon atoms; $R^3$ represents a branched or straight chain alkylene group having from 2 to 6 carbon atoms, a straight chain alkenylene group having from 4 to 6 carbon atoms, a straight chain alkynylene group having from 4 to 6 carbon atoms, an oxyalkylene group having from 5 to 8 carbon atoms, or a 1,4-phenylenedimethylene group; $Y^1$ and $Y^2$ each represents an oxygen atom or —NH—; X represents

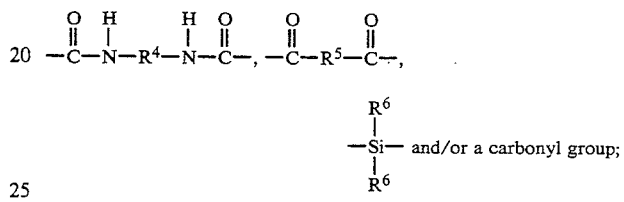

$R^4$ represents an alkylene group having from 1 to 10 carbon atoms, a substituted or unsubstituted phenylene group (e.g., phenylene, o-methylphenylene, m-methylphenylene, p-methylphenylene), a substituted or unsubstituted biphenylene group (e.g., biphenylene, 2,2'-dimethylphenylene, 3,3'-dimethylphenylene), or a substituted or unsubstituted methylenebiphenyl group (e.g., methylenebiphenyl, 2,2'-dimethylmethylenebiphenyl, 3,3'-dimethylmethylenebiphenyl); $R^5$ represents a single bond, an alkylene group having from 1 to 12 carbon atoms, an alkenylene group having from 4 to 12 carbon atoms, or a substituted or unsubstituted phenylene group (e.g., phenylene, 2-methylphenylene, 3-methylphenylene); $R^6$ represents an alkyl group having from 1 to 6 carbon atoms or a phenyl group; and m and n each represents 0 or an integer of from 1 to 20, provided that m and n do not simultaneously represent 0, and an optically active oligomer represented by formula (I):

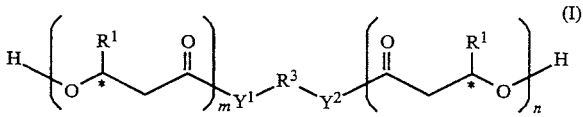

wherein $R^1$, $R^3$, $Y^1$, $Y^2$, m, and n are as defined above, which can be used as an intermediate for preparing the polymer represented by formula (II).

The optically active polymer represented by formula (II) can be prepared by a process comprising polycondensing the optically active oligomer represented by formula (I) with a diisocyanic acid ester represented by formula (VIII):

wherein $R^4$ is as defined above,
a dicarboxylic acid dichloride represented by formula (IX):

wherein $R^5$ is as defined above, a dicarboxylic acid dialkyl ester represented by formula (X):

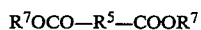

$$R^7OCO-R^5-COOR^7 \quad (X)$$

wherein $R^5$ is as defined above; and $R^7$ represents an alkyl group,
a dicarboxylic acid anhydride represented by formula (XI):

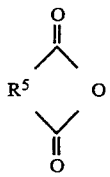

(XI)

wherein $R^5$ is as defined above,
a dichlorosilane represented by formula (XII):

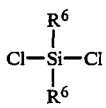

(XII)

wherein $R^6$ is as defined above,
and/or a dialkyl carbonate represented by formula (XIII):

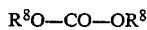

$$R^8O-CO-OR^8 \quad (XIII)$$

wherein $R^8$ represents an alkyl group.

The optically active oligomer represented by formula (I) can be prepared by polycondensing an (R)-3-hydroxyalkanoic acid ester represented by formula (III):

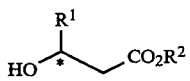

(III)

wherein $R^1$ is as defined above; and $R^2$ represents an alkyl group having from 1 to 6 carbon atoms,
with at least one compound represented by formula (IV):

$$H-Y^1-R^3-Y^2-H \quad (IV)$$

wherein $R^3$, $Y^1$, and $Y^2$ are as defined above

BRIEF DESCRIPTION OF THE DRAWING

The Figure is a graph showing the change of weight percent retention of the polymer with time.

DETAILED DESCRIPTION OF THE INVENTION

The oligomer which can be used as an intermediate for the polymer of the present invention can be prepared through, for example, the following reaction scheme:

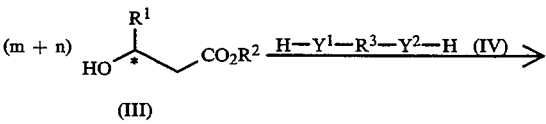

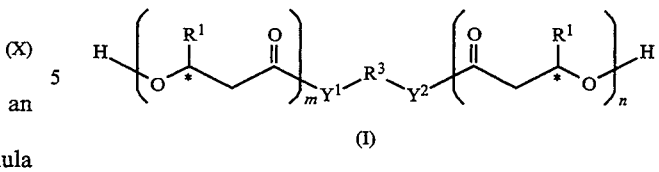

(I)

wherein $R^1$, $R^2$, $R^3$, $Y^1$, $Y^2$, m and n are as defined above.

The optically active 3-hydroxyalkanoic acid alkyl ester of formula (III) ((R)-3HA)), the starting compound used in the above reaction, is easily obtained by the process discovered by the same inventors of the present invention and disclosed in JP-A-63-310847 (the term "JP-A" as used herein means an "unexamined published Japanese patent application"), which comprises enantioselectively hydrogenating a β-keto ester of formula:

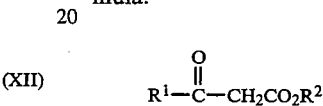

wherein $R^1$ represents an alkyl group having from 1 to 5 carbon atoms; and $R^2$ represents an alkyl group having from 1 to 6 carbon atoms, by using a ruthenium-optically active phosphine complex as a catalyst.

The reaction for obtaining the oligomer (I) can be carried out by charging the compound (IV), i.e., a diol, a diamine, or an amino alcohol, and (R)-3HA of (m+n) times the amount of the compound (IV) in a reaction vessel in an inert gas atmosphere, e.g., nitrogen or argon, adding a catalyst, when necessary, to the reaction vessel, distilling off methanol at 100° to 160° C. for 1 to 3 hours in a nitrogen stream, followed by gradually reducing the inner pressure to 0.1 from 1.0 mmHg at which the reaction is continued for 3 to 7 hours.

Where the compound of formula (IV) is a diamine ($Y^1=Y^2=NH$), no catalyst is necessary. Where the compound (IV) is a diol ($Y^1=Y^2=O$) or an amino alcohol (either one of $Y^1$ and $Y^2$ is O with the other being NH), a catalyst is needed. Examples of suitable catalysts to be used include (i) organotin compounds, such as dialkyltin oxides (e.g., dibutyltin oxide), trialkyltin alkoxides (e.g., tributyltin methoxide), tin alkyl acids (e.g., tin octylate), tetraphenyltin, and tetraallyltin, and (ii) organotitanium compounds, such as titanium alkoxides (e.g., titanium tetraisopropoxide). These catalysts may be used singly or, if desired, in combination of two or more thereof. The catalyst is used in an amount of from 1/500 to 1/100 mol per mole of the (R)-3HA.

The resulting oligomer may be purified by crystallization, but since the catalyst used in the preparation of the oligomer also serves in the subsequent copolymerization, the oligomer as produced may be subjected to the copolymerization without being purified.

The oligomer of formula (I) wherein m=n=1 can also be obtained by reacting the diol, diamine or amino alcohol of formula (IV) with double the equivalent of diketene and then enantioselectively hydrogenating the product in accordance with the process disclosed in JP-A-63-310847 supra.

The copolymerization reaction for obtaining the optically active polymer (II) can be carried out by charging the optically active oligomer (I) and the compound (VIII), (IX), (X), (XI), (XII), or (XIII) in a reaction vessel in an inert gas atmosphere, e.g., nitrogen or argon, and conducting copolymerization in the absence or presence of 2 to 10 times the amount of an inert organic solvent (e.g., toluene, benzene, anisole, dimethylformamide (DMF), dioxane, tetrahydrofuran (THF), dichloroethane, or methylene chloride), if necessary in the presence of a catalyst at a temperature of from 0° to 160° C. under normal pressure for a period of from 1 hour to 2 days. Where a dicarboxylic acid dichloride (IX) or a dichlorosilane (XII) is used, the reaction is carried out in the presence of an amine as a dehydrochlorinating agent.

Specific examples of the diisocyanic acid esters (VIII) include hexamethylene diisocyanate (HMDI), toluene 2,4-diisocyanate, 4,4′-diphenylmethane diisocyanate, o-xylylene diisocyanate, and m-toluidine diisocyanate.

Specific examples of the dicarboxylic acid dichlorides (IX) include terephthalic acid dichloride, adipic acid dichloride, succinic acid dichloride, oxalic acid dichloride, azelaic acid dichloride, fumaric acid dichloride, and phosgene.

Specific examples of the dicarboxylic acid dialkyl esters (X) include dimethyl terephthalate, dimethyl adipate, dimethyl succinate, dimethyl oxalate, dimethyl azelate, and dimethyl fumarate.

Specific examples of the dicarboxylic acid anhydrides (XI) include maleic anhydride, phthalic anhydride, succinic anhydride, and itaconic anhydride.

Specific examples of the dichlorosilanes (XII) include dimethyldichlorosilane, diethyldichlorosilane, dipropyldichlorosilane, dibutyldichlorosilane, and diphenyldi chlorosilane.

Specific examples of the dialkyl carbonates (XIII) include dimethyl carbonate.

Specific examples of the diols (IV) include ethylene glycol, 1,3-propanediol, 1,4-butanediol, 2,2-dimethyl-1,3-propanediol, cis-2-butene-1,4-diol, trans-2-butene-1,4-diol, 2-butyne-1,4-diol, 1,6-hexanediol, 1,10-decanediol, xylylene glycol, diethylene glycol, triethylene glycol, polyethylene glycol, polypropylene glycol, polytetramethylene glycol, and 1,4-phenylenedimethanol.

Specific examples of the diamines (IV) include hexamethylenediamine.

Specific examples of the amino alcohols (IV) include ethanolamine.

These compounds (IV) may be used individually or, if desired, in combination of two or more thereof.

Where the copolymerization is effected by using a diisocyanic acid ester (VIII) or by using a dicarboxylic acid dichloride (IX) or a dichlorosilane (XII) in the presence of an amine, no catalyst is needed. Where in using a dicarboxylic acid dialkyl ester (X), a dicarboxylic acid anhydride (XI), or a dialkyl carbonate (XIII), the reaction should be conducted in the presence of a catalyst. The catalyst to be used include those described above with respect to the reaction for obtaining the oligomer (I); i.e., (i) organotin compounds, such as dialkyltin oxides (e.g., dibutyltin oxide), trialkyltin alkoxides (e.g.,-tributyltin methoxide), tin alkyl acids (e.g., tin octylate), tetraphenyltin, and tetraallyltin, and (ii) organotitanium compounds, such as titanium alkoxides (e.g., titanium tetraisopropoxide) and titanium carboxylates (e.g., tetraoctyl titanate). These catalysts may be used individually or, if desired, in combination of two or more thereof. The catalyst is used in an amount of from 1/10 to 1/10000 mol per mole of the starting oligomer.

Examples of suitable amines which can be used in the reaction between the oligomer (I) and a dicarboxylic acid dichloride (IX) or a dichlorosilane (XII) include triethylamine, pyridine, and imidazole. The amine is usually used in an amount of from 1.5 to 3.0 mols per mol of the starting oligomer.

The oligomer represented by formula (I) of the present invention can be preferably produced at a temperature of from 120° to 140° C. and a reaction time of from 6 to 10 hours.

The oligomer represented by formula (I) has a number average molecular weight of from generally 400 to 2,500, preferably 500 to 2,000 and a weight-average molecular weight of from generally 500 to 4,000, preferably 600 to 2,500.

In the preparation of the polymer represented by formula (II) of the present invention, polyurethane can be preferably produced at a temperature of from 110° to 150° C. and a reaction time of from 5 to 8 hours. Further, in the preparation of polyester, the preferred reaction temperatures at polycondensation by removal of methanol or by acid chloride are from 130° to 140° C. and 25° to 45° C., respectively.

The polymer represented by formula (II) has a number average molecular weight of from generally 7,000 to 150,000, preferably 10,000 to 100,000 and a weight-average molecular weight of from generally 10,000 to 200,000, preferably 30,000 to 150,000.

According to the present invention, copolymerization of an optically active oligomer having an (R)-3HA unit and a monomer yields a novel functional polymer having biodegradability and hydrolyzability with ease and industrial advantage.

The present invention is now illustrated in greater detail with reference to Examples, Reference Example, and Test Examples, but it should be understood that the present invention is not construed as being limited thereto.

In analyses of the products obtained, the following apparatus were used.

NMR Spectrum: AM-400 (400 MHz), manufactured by Bruker, Inc.

IR Spectrum: IR-810 (infrared spectrophotometer), manufactured by JASCO Inc.

Differential Thermal Analysis: DSC 50 (differential scanning calorimeter), manufactured by Shimadzu Corporation Molecular Weight: D-2520 GPC Integrator, manufactured by Hitachi, Ltd.

Optical Rotation: DIP-360 (digital polarimeter), manufactured by JASCO Inc.

Mass Spectrum (MS): M-80B (mass spectrometer), manufactured by Hitachi, Ltd.

Chemical Purity: 263-80 (gas chromatograph), manufactured by Hitachi, Ltd.

Biodegradability tests of the products obtained were conducted in Takasago Research Institute by using activated sludge.

EXAMPLE 1
Synthesis of Methyl (R)-3-hydroxy-butyrate/1,4-Butanediol Oligomer

In a 200 ml reactor were charged 105.5 g (0.893 mol) of methyl (R)-3-hydroxybutyrate (hereinafter abbreviated as (R)-3HB), 8.05 g (0.0893 mol) of 1,4-butanediol, and 0.45 g (1.80 mmol) of dibutyltin oxide, and the mixture was distilled at 130° C. for 3 hours in a nitrogen stream to remove methanol. The pressure was gradually diminished to 0.5 mmHg, and the reaction mixture was stirred at 140° C. under that reduced pressure for 5 hours to obtain 76.8 g (percent yield: 90.4%) of the titled oligomer.

$^1$H-NMR (400 MHz, CDCl$_3$)δ(ppm):
 (R)-3HB Segment:
  1.22–1.33 (30H, m), 2.35–2.70 (20H, m), 4.16 (2H, m), 5.28 (8H, m)
 1,4-Butanediol Segment:
  1.71 (4H, m), 4.11 (4H, m)
IR (liquid film, cm$^{-1}$): 3500, 2980, 1740, 1385, 1305, 1190
Weight-Average Molecular Weight (Mw): 920
Number-Average Molecular Weight (Mn): 700
Melting Point (Tm): 89.0° C.

EXAMPLE 2

Synthesis of (R)-3HB/1,4.Butanediol Oligomer

In a 500 ml reactor were charged 250 g (2.12 mol) of (R)-3HB, 9.53 g (0.106 mol) of 1,4-butanediol, and 1.05 g (4.2 mmol) of dibutyltin oxide, and the mixture was allowed to react in the same manner as in Example 1 to obtain 181.6 g (percent yield: 96.4%) of the titled oligomer.

$^1$H-NMR (400 MHz, CDCl$_3$)δ(ppm):
 (R)-3HB Segment:
  1.22–1.33 (60H, m), 2.35–2.70 (40H, m), 4.16 (2H, m), 5.28 (18H, m)
 1,4-Butanediol Segment:
  1.71 (4H, m), 4.11 (4H, m)
IR (liquid film, cm$^{-1}$): 3500, 2980, 1740, 1385, 1305, 1190
Mw: 1,640
Mn: 1,060
Tm: 120.0° C.

EXAMPLE 3

Synthesis of (R)-3HB/2,2-Dimethyl-1,3-propanediol Oligomer

In a reactor were charged 105.5 g (0.893 mol) of (R)-3HB, 9.30 g (0.0893 mol) of 2,2-dimethyl-1,3-propanediol, and 0.74 g (3.0 mmol) of dibutyltin oxide, and the mixture was allowed to react in the same manner as in Example 1 to obtain 82.8 g (percent yield: 96.8%) of the titled oligomer.

$^1$H-NMR (400 MHz, CDCl$_3$)δ(ppm):
 (R)-3HB Segment:
  1.22–1.33 (30H, m), 2.35–2.70 (20H, m), 4.19 (2H, m), 5.27 (8H, m)
 2,2-Dimethyl-1,3-propanediol Segment:
  0.86–1.00 (6H, m), 3.90 (4H, m)
IR (liquid film, Cm$^{-1}$): 3500, 2980, 1740, 1385, 1305, 1190
Mw: 1,100
Mn: 810
Tm: 70.3° C.

EXAMPLE 4

Synthesis of (R)-3HB/2,2-Dimethyl-1,3-propanediol Oligomer

In a reactor were charged 105.5 g (0.893 mol) of (R)-3HB, 4.65 g (0.0447 mol) of 2,2-dimethyl-1,3-propanediol, and 0.45 g (1.80 mmol) of dibutyltin oxide, and the mixture was allowed to react in the same manner as in Example 1 to obtain 79.0 g (percent yield: 96.9%) of the titled oligomer.

$^1$H-NMR (400 MHz, CDCl$_3$)δ(ppm):
 (R)- 3HB Segment:
  1.22–1.33 (60H, m), 2.35–2.70 (40H, m), 4.19 (2H, m), 5.27 (18H, m)
 2,2-Dimethyl-1,3-propanediol Segment:
  0.86–1.00 (6H, m), 3.90 (4H, m)
IR (liquid film, cm$^{-1}$): 3500, 2980, 1740, 1385, 1305, 1190
Mw: 1,870
Mn: 1,400
Tm: 124.9° C.

EXAMPLE 5

Synthesis of (R)-3HB/cis-2-Butene-1,4-diol Oligomer

In a reactor were charged 118.1 g (1.0 mol) of (R)-3HB, 8.81 g (0.1 tool) of cis-2-butene-1,4-diol, and 0.5 g (2.0 mmol) of dibutyltin oxide, and the mixture was allowed to react in the same manner as in Example 1 to obtain 86.7 g (percent yield: 90.4%) of the titled oligomer.

$^1$H-NMR (400 MHz, CDCl$_3$)δ(ppm):
 (R)-3HB Segment:
  1.22–1.33 (30H, m), 2.40–2.70 (20H, m), 5.18–5.36 (SH, m)
 cis-2-Butene-1,4-diol Segment:
  4.65–4.75 (4H, m), 5.74 (2H, mm)
IR (liquid film, cm$^{-1}$): 3500, 2980, 1740, 1385, 1305, 1190
Mw: 870
Mn: 670
Tm: 85.4° C.

EXAMPLE 6

Synthesis of (R)-3HB/cis-2-Butene-1,4-diol Oligomer

In a reactor were charged 100 g (0.847 mol) of (R)-3HB, 3.70 g (0.042 mol) of cis-2-butene-1,4-diol, and 0.7 g (2.8 mmol) of dibutyltin oxide, and the mixture was allowed to react in the same manner as in Example 1 to obtain 69.4 g (percent yield: 87.3%) of the titled oligomer.

$^1$H-NMR (400 MHz, CDCl$_3$)δ(ppm):
 (R)-3HB Segment:
  1.22–1.33 (60H, m), 2.35–2.70 (40H, m), 4.19 (2H, m), 5.27 (18H, m)
 cis-2-Butene-1,4-diol Segment:
  4.65–4.75 (4H, m), 5.74 (2H, mm)
IR (liquid film, cm$^{-1}$): 3500, 2980, 1740, 1385, 1305, 1190
Mw: 1,500
Mn: 980
Tm: 120.5° C.

EXAMPLE 7

Synthesis of (R}-3HB/2-Butyne-1,4-diol Oligomer

In a reactor were charged 70.9 g (0.6 mol) of (R) - 3HB, 8.61 g (0.1 mol) of 2-butyne-1,4-diol, and 0.5 g (2.0 mmol) of dibutyltin oxide, and the mixture was allowed to react in the same manner as in Example 1 to obtain 55.0 g (percent yield: 90.5%) of the titled oligomer.

$^1$H-NMR (400 MHz, CDCl$_3$)δ(ppm):
 (R)-3HB Segment:
  1.22–1.33 (18H, m), 2.35–2.70 (12H, m), 4.19 (2H, m), 5.27 (4H, m)
 2-Butyne-1,4-diol Segment:
  4.68–4.78 (4H, m)
IR (liquid film, cm$^{-1}$): 3500, 2980, 1740, 1385, 1305, 1190
Mw: 780
Mn: 550
Tm: 81.1° C.

EXAMPLE 8

Synthesis of (R)-3HB/2-Butyne-1,4-diol Oligomer

In a reactor were charged 118.1 g (1.0 mol) of (R)-3HB, 4.30 g (0.05 tool) of 2-butyne-1,4-diol, and 0.5 g (2.0 mmol) of dibutyltin oxide, and the mixture was allowed to react in the same manner as in Example 1 to obtain 71.0 g (percent yield: 77.7%) of the titled oligomer.

$^1$H-NMR (400 MHz, CDCl$_3$)δ(ppm):
  (R)-3HB Segment:
    1.22–1.33 (60H, m), 2.35–2.70 (40H, m), 4.19 (2H, m), 5.27 (18H, m)
  2-Butyne-1,4-diol Segment:
    4.68–4.78 (4H, m)
IR (liquid film, cm$^{-1}$): 3500, 2980, 1740, 1385, 1305, 1190
Mw: 1,660
Mn: 1,010
Tm: 123.2° C.

EXAMPLE 9

Synthesis of (R)-3HB/(R)-3-Hydroxyvaleric Acid/1,4-Butanediol Oligomer

In a reactor were charged 104.89 g (0.889 mol) of (R)-3HB, 29.3 g (0.222 mol) of (R)-3-hydroxyvaleric acid (hereinafter abbreviated as (R)-3HV), 5.0 g (0.0556 mol) of 1,4-butanediol, and 0.55 g (2.22 mmol) of dibutyltin oxide, and the mixture was allowed to react in the same manner as in Example 1 to obtain 101.9 g (percent yield: 98.3%) of the titled oligomer.

$^1$H-NMR (400 MHz, CDCl$^3$)δ(ppm):
  (R)-3HB Segment:
    1.22–1.33 (48H, m), 2.35–2.70 (32H, m), 4.16 (m), 5.20–5.35 (m)
  (R)-3HV Segment:
    0.85–1.00 (12H, m), 1.63 (8H, m), 2.35–2.70 (8H, m), 4.16 (m), 5.17 (m)
  1,4-Butanediol Segment:
    1.70 (4H, m), 4.10 (4H, m)
IR(liquid film, cm$^{-1}$): 3500, 2980, 1740, 1385, 1305, 1190
Mw: 1,320
Mn: 910
Tm: 77.0° C.

EXAMPLE 10

Synthesis of (R)-3HB/Diethylene Glycol Oligomer

In a reactor were charged 118.1 g (1.0 mol) of (R)-3HB, 10.6 g (0.1 mol) of diethylene glycol, and 0.5 g (2.0 mmol) of dibutyltin oxide, and the mixture was allowed to react in the same manner as in Example 1 to obtain 89.6 g (percent yield: 92.8%) of the titled oligomer.

$^1$H-NMR (400 MHz, CDCl$_3$)δ(ppm):
  (R)-3HB Segment:
    1.18–1.36 (30H, m), 2.35–2.72 (20H, m), 4.19 (m), 5.20–5.35 (m)
  Diethylene Glycol Segment:
    3.65–3.76 (m), 4.21–4.31 (m)
IR(liquid film, cm$^{-1}$): 3530, 2980, 1740, 1190
Mw: 1,110
Mn: 800
Tm: 77.5° C.

EXAMPLE 11

Synthesis of (R)-3HB/Triethylene Glycol Oligomer

In a reactor were charged 118.1 g (1.0 mol) of (R)-3HB, 15.0 g (0.1 mol) of triethylene glycol, and 0.5 g (2.0 mmol) of dibutyltin oxide, and the mixture was allowed to react in the same manner as in Example 1 to obtain 92.4 g (percent yield: 91.5%) of the titled oligomer.

$^1$H-NMR (400 MHz, CDCl$_3$)δ(ppm):
  (R)-3HB Segment:
    1.18–1.36 (30H, m), 2.35–2.72 (20H, m), 4.19 (m), 5.20–5.35 (m)
  Triethylene Glycol Segment:
    3.58 (m), 4.22–4.30 (m)
IR(liquid film, cm$^{-1}$): 3500, 2980, 1740, 1190
Mw: 1,090
Mn: 910
Tm: 94.4° C.

REFERENCE EXAMPLE

Synthesis of 4,11-Dicarbonyl-5,10-dioxy-2,13-tetradecanedione

Diketene (25.2 g, 0.3 mol) was added dropwise to a solution of 13.5 g (0.15 mol) of 1,4-butanediol and three drops of triethyl amine in 40 ml of methylene chloride at 10° to 20° C., and the mixture was stirred at room temperature for 2 days. The solution was washed with a sodium hydrogencarbonate aqueous solution followed by concentration under reduced pressure. The concentrate was purified by column chromatography to obtain 31.0 g (percent yield: 80%) of the titled compound.

EXAMPLE 12

Synthesis of (2R,13R)-4,11-Dicarbonyl-5,10-dioxy-2,13-tetradecanediol

The 4,11-dicarbonyl-5,10-dioxy-2,13-tetradecanedione prepared in Reference Example (1335 g, 5.17 mol), 24.1 g (13.8 mmol) of Ru$_2$Cl$_4$((+)-T-BINAP)$_2$Et$_3$N (wherein (+)-T-BINAP represents (+)-2,2'-bis(di-p-tolylphosphino)-1,1'-binaphthyl; and Et represents ethyl), and 5.3 l of methylene chloride were allowed to react at a hydrogen pressure of 50 kg/m$^2$ for 10 hours (JP-A-63-310847). The resulting reaction mixture was treated with activated carbon, and methylene chloride was removed by distillation. The residue was subjected to distillation to obtain 1330 g (percent yield: 98.2%) of the titled oligomer.

$^1$H-NMR (400 MHz, CDCl$_3$)δ(ppm):
  1.24 (6H, d, J=6.3Hz), 1.73 (4H, m), 2.43 (2H, dd, J=16.4Hz, 8.6Hz), 2.50 (2H, dd, J=16.4Hz, 3.7Hz), 2.88 (2H, s), 4.14 (4H, m), 4.15-4.25 (2H, m)
$^{13}$C-NMR (100 MHz, CDCl$_3$)δ(ppm):
  22.5, 25.2, 42.8, 64.1, 64.3, 172.8
IR(liquid film, cm$^{-1}$): 3410, 2970, 1735, 1180
MS (m/z): 262 (M+)
$[α]_D = -180.0°$ (c=1.7, MeOH, 20° C.)

EXAMPLE 13

Synthesis of N,N'-(R)-3-hydroxybutanehexamethylenediamide

In a 200 ml reactor were charged 23.6 g (0.2 mol) of (R)-3HB and 11.6 g (0.1 mol) of hexamethylenediamine, and the mixture was gradually heated in a nitrogen stream to 130° to 140° C., at which the mixture was allowed to react for 5 hours while removing methanol. After cooling, the reaction mixture was dissolved in toluene, washed with water and then with a sodium hydrogencarbonate aqueous solution, and dried over magnesium sulfate to obtain 29 g of a crude product. Recrystallization of the crude product gave 24.3 g (percent yield: 84.3%) of the titled compound.

¹H-NMR (400 MHz, CDCl₃)δ(ppm):
   1.24 (6H, d, J=6.3Hz), 1.36 (4H, m), 1.51 (4H, m),
   2.26 (2H, dd, J=15.2Hz, 8.8Hz), 2.35 (2H, dd,
   J=15.2Hz, 2.9Hz), 3.26 (4H, m), 4.18 (2H, ddd,
   J=8.8Hz, 6.3Hz, 2.9Hz), 6.09 (2H, s)
¹³C-NMR (100 MHz, CDCl₃)δ(ppm):
   23.0, 25.7, 29.2, 38.8, 44.1, 64.9, 172.5
IR(liquid film, cm⁻¹): 3300, 2925, 2860, 1640, 1550
MS (m/z): 288 (M+)
[α]= −38.0° (c=0.75, CHCl₃, 20° C.)

EXAMPLE 14

Synthesis of Polyester-polyurethane In a 200 ml reactor was charged 23.23 g (25.5 mmol) of the oligomer obtained in Example 1 in a nitrogen atmosphere, and a half of 4.29 g (25.5 mmol) of hexamethylene diisocyanate (HMDI) was added thereto dropwise at 120° C., followed by stirring for 2 hours. The rest of HMDI was added thereto dropwise over 4 hours at 120 to 150° C. The crude polymer thus produced was dissolved in 50 ml of chloroform, and 500 ml of diethyl ether was added thereto to form a precipitate. The precipitate was collected by filtration and washed with 500 ml of n-hexane to obtain 21.27 g (percent yield: 74.6%) of polyester-polyurethane.

¹H-NMR (400 MHz, CDCl₃)δ(ppm):
   (R)-3HB Segment:
      1.22–1.30 (30H, m), 2.40–2.70 (20H, m), 5.05–5.33 (10H, m)
   1,4-Butanediol Segment:
      1.70 (4H, m), 4.10 (4H, m)
   HMDI Segment:
      1.32 (4H, m), 1.48 (4H, m), 3.14 (4H, m), 4.89 (2H, s)
Mw: 60,400
Mn: 32,400

EXAMPLE 15

Synthesis of Polyester-polyurethane

In the same manner as in Example 14, except for starting with 7.31 g (3.95 mmol) of the oligomer obtained in Example 2 and 0.664 g (3.95 mmol) of HMDI, 7.38 g (percent yield: 92.6%) of polyester-polyurethane was obtained.

¹H-NMR (400 MHz, CDCl₃)δ(ppm):
   (R)-3HB Segment:
      1.22–1.30 (60H, m), 2.40–2.70 (40H, m), 5.05–5.33 (20H, m)
   1,4-Butanediol Segment:
      1.70 (4H, m), 4.10 (4H, m)
   HMDI Segment:
      1.32 (4H, m), 1.48 (4H, m), 3.14 (4H, m), 4.89 (2H, s)
Mw: 54,100
Mn: 27,700

EXAMPLE 16

Synthesis of Polyester-polyurethane

In the same manner as in Example 14, except for starting with 24.07 g (24.94 mmol) of the oligomer obtained in Example 3 and 4.20 g (24.94 mmol) of HMDI, 23.91 g (percent yield: 84.6%) of polyester-polyurethane was obtained.

¹H-NMR (400 MHz, CDCl₃)δ(ppm):
   (R)-3HB Segment:
      1.22–1.30 (30H, m), 2.40–2.70 (20H, m), 5.05–5.33 (10H, m)
   2,2-Dimethyl-1,3-propanediol Segment:
      0.86–1.00 (6H, m), 3.90 (4H, m)
   HMDI Segment:
      1.32 (4H, m), 1.48 (4H, m), 3.14 (4H, m), 4.89 (2H, s)
Mw: 66,700
Mn: 39,600

EXAMPLE 17

Synthesis of Polyester-polyurethane

In the same manner as in Example 14, except for starting with 20.1 g (10.98 mmol) of the oligomer obtained in Example 4 and 1.85 g (10.98 mmol) of HMDI, 20.48 g (percent yield: 93.5%) of polyester-polyurethane was obtained.

¹H-NMR (400 MHz, CDCl₃)δ(ppm):
   (R)-3HB Segment:
      1.22–1.30 (30H, m), 2.40–2.70 (20H, m), 5.05–5.33 (10H, m)
   2,2-Dimethyl-1,3,propanediol Segment:
      0.86–1.00 (6H, m), 3.90 (4H, m)
   HMDI Segment:
      1.32 (4H, m), 1.48 (4H, m), 3.14 (4H, m), 4.89 (2H, s)
Mw: 44,100
Mn: 21,600

EXAMPLE 18

Synthesis of Polyester-polyurethane

In the same manner as in Example 14, except for starting with 38.08 g (40 mmol) of the oligomer obtained in Example 5 and 6.73 g (40 mmol) of HMDI, 40.1 g (percent yield: 88.2%) of polyester-polyurethane was obtained.

¹H-NMR (400 MHz, CDCl₃)δ(ppm):
   (R)-3HB Segment:
      1.22–1.30 (30H, m), 2.40–2.70 (20H, m), 5.05–5.33 (10H, m)
   cis-2-Butene-1,4-diol Segment:
      4.62–4.73 (4H, m), 5.74 (2H, mm)
   HMDI Segment:
      1.32 (4H, m), 1.48 (4H, m), 3.14 (4H, m), 4.89 (2H, s)
Mw: 49,300
Mn: 24,300

EXAMPLE 19

Synthesis of Polyester-polyurethane

In the same manner as in Example 14, except for starting with 20.25 g (13.5 mmol) of the oligomer obtained in Example 6 and 2.27 g (13.5 mmol) of HMDI, 20.0 g (percent yield: 89.8%) of polyester-polyurethane was obtained.

¹H-NMR (400 MHz, CDCl₃)δ(ppm):
   (R)-3HB Segment:
      1.22–1.30 (30H, m), 2.40–2.70 (20H, m), 5.05–5.33 (10H, m)
   cis-2-Butene-1,4-diol Segment:
      4.62–4.73 (4H, m), 5.74 (2H, mm)
   HMDI Segment:
      1.32 (4H, m), 1.48 (4H, m), 3.14 (4H, m), 4.89 (2H, s)
Mw: 41,800
Mn: 20,600

EXAMPLE 20

Synthesis of Polyester-polyurethane

In the same manner as in Example 14, except for starting with 26.67 g (44.3 mmol) of the oligomer obtained in Example 7 and 7.45 g (44.3 mmol) of HMDI, 30.7 g(percent yield: 89.0%) of polyester-polyurethane was obtained.

$^1$H-NMR (400 MHz, CDCl$_3$)δ(ppm):
  (R)-3HB Segment:
    1.22–1.30 (30H, m), 2.40–2.73 (20H, m), 5.05–5.33 (10H, m)
  2-Butyne-1,4-diol Segment:
    4.72 (4H, s)
  HMDI Segment:
    1.32 (4H, m), 1.48 (4H, m), 3.14 (4H, m), 4.89 (2H, s)
Mw: 70,900
Mn: 43,400

EXAMPLE 21

Synthesis of Polyester-polyurethane

In the same manner as in Example 14, except for starting with 30.6 g (16.93 mmol) of the oligomer obtained in Example 8 and 2.85 g (16.93 mmol) of HMDI, 28.7 g (percent yield: 85.1%) of polyester-polyurethane was obtained.

$^1$H-NMR (400 MHz, CDCl$_3$)δ(ppm):
  (R)-3HB Segment:
    1.22–1.30 (30H, m), 2.40–2.73 (20H, m), 5.05–5.33 (10H, m)
  2-Butyne-1,4-diol Segment:
    4.72 (4H, s)
  HMDI Segment:
    1.32 (4H, m), 1.48 (4H, m), 3.14 (4H, m), 4.89 (2H, s)
Mw: 32,100
Mn: 17,400

EXAMPLE 22

Synthesis of Polyester-polyurethane

In the same manner as in Example 14, except for starting with 15.3 g (10.1 mmol) of the oligomer obtained in Example 9 and 1.70 g (10.1 mmol) of HMDI, 15.4 g (percent yield: 90.6%) of polyester-polyurethane was obtained.

$^1$H-NMR (400 MHz, CDCl$_3$)δ(ppm):
  (R)-3HB Segment:
    1.22–1.36 (48H, m), 2.40–2.73 (32H, m), 5.20–5.35 (m)
  (R)-3HV Segment:
    0.82–0.97 (12H, m), 1.58–1.67 (8H, m), 2.40–2.70 (8H, m), 5.07–5.20 (m)
  1,4-Butanediol Segment:
    1.70 (4H, m), 4.10 (4H, m)
  HMDI Segment:
    1.32 (4H, m), 1.48 (4H, m), 3.14 (4H, m)
Mw: 32,300
Mn: 19,000

EXAMPLE 23

Synthesis of Polyester

In a 200 ml reactor were charged 20 g (21.1 mmol) of the oligomer obtained in Example 1, 4.09 g (21.07 mmol) of dimethyl terephthalate, and 0.06 g (0.21 mmol) of titanium tetraisopropoxide. The mixture was heated to 140° C. in a nitrogen stream for 3 hours to remove methanol. The inner pressure was gradually reduced, and the reaction mixture was stirred at 140° C. at 1 mmHg for 7 hours and then at 10$^{-3}$ mmHg for 7 hours to obtain 12.7 g (percent yield: 55.7%) of polyester.

$^1$H-NMR (400 MHz, CDCl$_3$)δ(ppm):
  (R)-3HB Segment:
    1.15–1.50 (30H, m), 2.35–2.87 (20H, m), 5.17–5.60 (10H, m)
  1,4-Butanediol Segment:
    1.60–2.00 (4H, m), 4.00–4.50 (4H, m)
  Terephthalic Acid Segment:
    8.02–8.14 (4H, m)
Mw: 17,400
Mn: 11,500

EXAMPLE 24

Synthesis of Polyester

In a 200 ml reactor were charged 10 g (10.5 mmol) of the oligomer obtained in Example 1, 2.08 g (26.3 mmol) of pyridine, and 40 ml of methylene chloride. To the mixture was further added at room temperature 2.14 g (10.5 mmol) of terephthalic acid dichloride, and the mixture was stirred at reflux for 18 hours. The reaction mixture was poured into water for liquid-liquid separation, washed with water, and concentrated. The concentrate was purified with diethyl ether to obtain 8.65 g (percent yield: 75.5%) of polyester.

$^1$H-NMR (400 MHz, CDCl$_3$)δ(ppm):
  (R)-3HB Segment:
    1.15–1.50 (30H, m), 2.35–2.87 (20H, m), 5.17–5.60 (10H, m)
  1,4-Butanediol Segment:
    1.60–2.00 (4H, m), 4.00–4.50 (4H, m)
  Terephthalic Acid Segment:
    8.02–8.14 (4H, m)
Mw: 30,000
Mn: 15,400

EXAMPLE 25

Synthesis of Polyester

In a 200 ml reactor were charged 10 g (10.5 mmol) of the oligomer obtained in Example 1, 2.65 g (26.2 mmol) of triethylamine, and 40 ml of methylene chloride. To the mixture was further added dropwise at room temperature 1.35 g (10.5 mmol) of dimethyldichlorosilane, and the mixture was stirred at reflux for 18 hours. The reaction mixture was poured into water for liquid-liquid separation, washed with water, and concentrated. The concentrate was purified with diethyl ether to obtain 8.00 g (percent yield: 75.5%) of polyester.

$^1$H-NMR (400 MHz, CDCl$_3$)δ(ppm):
  (R)-3HB Segment:
    1.20–1.35 (30H, m), 2.30–2.70 (20H, m), 4.30–4.40 (20H, m), 5.20–5.35 (8H, m)
  1,4-Butanediol Segment:
    1.70 (4H, m), 4.10 (4H, m)
  Dimethylsilane Segment:
    0.05–0.15 (6H, m)
Mw: 14,500
Mn: 7,600

The DSC data of the polymers obtained in Example 14 to 25 are shown in Table 1 below.

TABLE 1

| Example No. | Glass Transition Point (°C.) | Melting Point (°C.) | Decomposition Point (°C.) |
| --- | --- | --- | --- |
| 14 | −5 | 78 | 262 |
| 15 | 1 | 118 | 268 |
| 16 | 1 | 74 | 266 |
| 17 | 4 | 120 | 275 |
| 18 | −3 | 80 | 272 |
| 19 | 1 | 117 | 269 |
| 20 | 10 | — | 258 |

TABLE 1-continued

| Example No. | Glass Transition Point (°C.) | Melting Point (°C.) | Decomposition Point (°C.) |
| --- | --- | --- | --- |
| 21 | 5 | 120 | 274 |
| 22 | −3 | 87 | 270 |
| 23 | −14 | 88 | 292 |
| 24 | −19 | 78 | 290 |

TEST EXAMPLE 1

Biodegradability of Polymer of Example 16

Acclimatized (aerobic) sludge of return sludge supplied from the Hiratsuka Factory of Takasago International Corporation was used as a dispersion under conditions of 500 ppm (600 ml), pH 6.0–7.0, and 30° C.

A cast film of the polymer obtained in Example 16 measuring 1 cm×2 cm×0.05–0.1 mm was prepared by dissolved the polymer in a solvent (e.g., methylene chloride or chloroform), casting the solution in a petri dish, and evaporating the solvent.

The cast film weighing from 20 to 30 mg was put in a 50 ml flask together with the sludge dispersion, and the flask was placed in a shaking thermostatic water tank (manufactured by TAITEC Co., Ltd.) for up to 4 weeks. The polymer was weighed to obtain a percent retention with time. The results obtained are shown in the Fig. It is seen that the polymer film had undergone 33% degradation in 4 weeks.

TEST EXAMPLE 2

Biodegradability of Polymer of Example 18

The polymer obtained in Example 18 was tested in the same manner as in Test Example 1. The results obtained are shown in the Fig. It is seen that the polymer film had undergone 18% degradation in 4 weeks.

TEST EXAMPLE 3

Biodegradability of Polymer of Example 18

The polymer obtained in Example 20 was tested in the same manner as in Test Example 1. The results obtained are shown in the Fig. It is seen that the polymer film had undergone 7% degradation in 4 weeks.

While the invention has been described in detail and with reference to specific examples thereof, it will be apparent to one skilled in the art that various changes and modifications can be made therein without departing from the spirit and scope thereof.

What is claimed is:

1. An optically active polymer comprising a 3-hydroxyalkanoic acid ester unit represented by formula (II):

$$\left[\left(O^*\underset{m}{\overset{R^1}{\diagdown}}\underset{Y^1}{\overset{O}{\diagdown}}\right)R^3\diagdown Y^2\left(\underset{n}{\overset{O}{\diagdown}}\overset{R^1}{\diagdown}O\right)\right]X \quad (II)$$

wherein $R^1$ represents an alkyl group having from 1 to 5 carbon atoms; $R^3$ represents a branched or straight chain alkylene group having from 2 to 6 carbon atoms, a straight chain alkenylene group having from 4 to 6 carbon atoms, a straight chain alkynylene group having from 4 to 6 carbon atoms, an oxyalkylene group having from 5 to 8 carbon atoms, or a 1,4-phenylenedimethylene group; $Y^1$ and $Y^2$ each represent an oxygen atom; X represents $$-\overset{O}{\underset{\|}{C}}-\overset{H}{\underset{|}{N}}-R^4-\overset{H}{\underset{|}{N}}-\overset{O}{\underset{\|}{C}}-,$$

$R^4$ represents an alkylene group having from 1 to 10 carbon atoms, a substituted or unsubstituted phenylene group, a substituted or unsubstituted biphenylene group, or a substituted or unsubstituted methylenebiphenyl group; and m and n each represents zero or an integer of from 1 to 20, provided that m and n do not simultaneously represent zero.

2. A process for producing an optically active polymer comprising a 3-hydroxyalkanoic acid ester unit represented by formula (II):

$$\left[\left(O^*\underset{m}{\overset{R^1}{\diagdown}}\underset{Y^1}{\overset{O}{\diagdown}}\right)R^3\diagdown Y^2\left(\underset{n}{\overset{O}{\diagdown}}\overset{R^1}{\diagdown}O\right)\right]X \quad (II)$$

wherein $R^1$ represents an alkyl group having from 1 to 5 carbon atoms; $R^3$ represents a branched or straight chain alkylene group having from 2 to 6 carbon atoms, a straight chain alkenylene group having from 4 to 6 carbon atoms, a straight chain alkynylene group having from 4 to 6 carbon atoms, an oxyalkylene group having from 5 to 8 carbon atoms, or a 1,4-phenylenedimethylene group; $Y^1$ and $Y^2$ each represent an oxygen atom; X represents $$-\overset{O}{\underset{\|}{C}}-\overset{H}{\underset{|}{N}}-R^4-\overset{H}{\underset{|}{N}}-\overset{O}{\underset{\|}{C}}-,$$

$R^4$ represents an alkylene group having from 1 to 10 carbon atoms, a substituted or unsubstituted phenylene group, a substituted or unsubstituted biphenylene group, or a substituted or unsubstituted methylenebiphenyl group; and m and n each represents zero or an integer of from 1 to 20, provided that m and n do not simultaneously represent zero, comprising polycondensing an optically active oligomer represented by formula (I):

$$H\left[\left(O^*\underset{m}{\overset{R^1}{\diagdown}}\underset{Y^1}{\overset{O}{\diagdown}}\right)R^3\diagdown Y^2\left(\underset{n}{\overset{O}{\diagdown}}\overset{R^1}{\diagdown}O\right)\right]H \quad (I)$$

wherein $R^1$, $R^3$, $Y^1$ $Y^2$, m and n are as defined above, with a diisocyanic acid ester represented by formula (VIII):

$$O=C=N-R^4-N=C=O \quad (VIII)$$

wherein $R^4$ is as defined above.

* * * * *